(12) United States Patent
Lee et al.

(10) Patent No.: US 11,389,568 B2
(45) Date of Patent: Jul. 19, 2022

(54) TYROSINE PEPTIDE CROSS-LINKED BIOCOMPATIBLE HYDROGEL AND METHOD OF PRODUCTION

(71) Applicant: SEOUL NATIONAL UNIVERSITY R&DB FOUNDATION, Seoul (KR)

(72) Inventors: Yoon Sik Lee, Anyang-si (KR); Byung Gee Kim, Seoul (KR); Sung Jun Park, Seoul (KR); Sang Hyuk Lee, Gunpo-si (KR)

(73) Assignee: Science@Home Inc., Seoul (KR)

( * ) Notice: Subject to any disclaimer, the term of this patent is extended or adjusted under 35 U.S.C. 154(b) by 111 days.

(21) Appl. No.: 16/396,881

(22) Filed: Apr. 29, 2019

(65) Prior Publication Data
US 2019/0314556 A1 Oct. 17, 2019

Related U.S. Application Data

(63) Continuation of application No. PCT/KR2016/011973, filed on Oct. 27, 2017.

(30) Foreign Application Priority Data

Oct. 27, 2016 (KR) .................. 10-2016-0141147

(51) Int. Cl.
| | | |
|---|---|---|
| *A61L 27/52* | (2006.01) | |
| *A61L 27/18* | (2006.01) | |
| *A61L 27/20* | (2006.01) | |
| *A61L 27/54* | (2006.01) | |
| *A61K 38/08* | (2019.01) | |
| *C07K 7/06* | (2006.01) | |

(52) U.S. Cl.
CPC .............. *A61L 27/52* (2013.01); *A61K 38/08* (2013.01); *A61L 27/18* (2013.01); *A61L 27/20* (2013.01); *A61L 27/54* (2013.01); *C07K 7/06* (2013.01); *A61L 2300/414* (2013.01)

(58) Field of Classification Search
None
See application file for complete search history.

(56) References Cited

U.S. PATENT DOCUMENTS

2016/0256604 A1  9/2016 Hanna et al.

FOREIGN PATENT DOCUMENTS

| KR | 1020100076173 A | 7/2010 |
|---|---|---|
| KR | 1020160026441 A | 3/2016 |
| KR | 1020160051839 A | 5/2016 |
| PT | 107426 A | 4/2014 |

(Continued)

OTHER PUBLICATIONS

Christopher M. Elvin et al, A highly elastic tissue sealant based on photopolymerised gelatin, Biomaterials, Aug. 1, 2010, vol. 31, pp. 8323-8331, Elsevier, Amsterdam, Netherlands.

(Continued)

*Primary Examiner* — Kevin S Orwig
(74) *Attorney, Agent, or Firm* — STIP Law Group, LLC

(57) ABSTRACT

The present invention relates to a biopolymer-based hydrogel as a functional biomaterial produced by crosslinking in the presence of a photopolymerization initiator. The hydrogel of the present invention is elastic so as to be adapted to various shapes in both in vivo and in vitro applications. It is biocompatible, achieving maximum effects on wound healing as wound dressing and tissue adhesion preventing material. The present invention also relates to a method for producing the biocompatible hydrogel.

8 Claims, 14 Drawing Sheets

Specification includes a Sequence Listing.

(56) References Cited

FOREIGN PATENT DOCUMENTS

WO  WO2011002249 A2  1/2011
WO  WO2011059326 A2  5/2011

OTHER PUBLICATIONS

Motoichi Kurisawa et al, Injectable biodegradable hydrogels composed of hyaluronic acid-tyramine conjugates fordrug delivery and tissue engineering, ChemComm, Jul. 28, 2005, pp. 4312-4314, See p. 4312 and Schemes 1-2.The Royal Science of Chemistry, London, United Kingdom.
Yin Ding et al, Photo-Cross-Linking Approach to Engineering Small Tyrosine-Containing Peptide Hydrogels with Enhanced Mechanical Stability, Langmuir, Oct. 4, 2013, pp. 13299-13306, vol. 29, See abstract and figure1, American Chemical Society, Washington DC, USA.
Park, Sung Joon et al., "(2P-279)Riboflavin-sensilized Photo-crosslinked Hyaluronic Acid Hydrogel as a Wound Healing Agent", 2016 KSIEC Fail Meeting, Poster presentation, Oct. 28, 2016, p. 304, The Korean Society of Industrial and Engineering Chemistry, Seoul, Republic of Korea.
International Search Report of PCT/KR2017/011973, dated Feb. 5, 2018, English translation.
Nicole R. Raia et al, Enzymatically crosslinked silk-hyaluronic acid hydrogels, Biomaterials, Mar. 27, 2017, pp. 58-67,vol. 131, Elsevier, Amsterdam, Netherland.
The extended European Search Report of 17 865 790.4, dated May 26, 2020.

[Fig. 5]
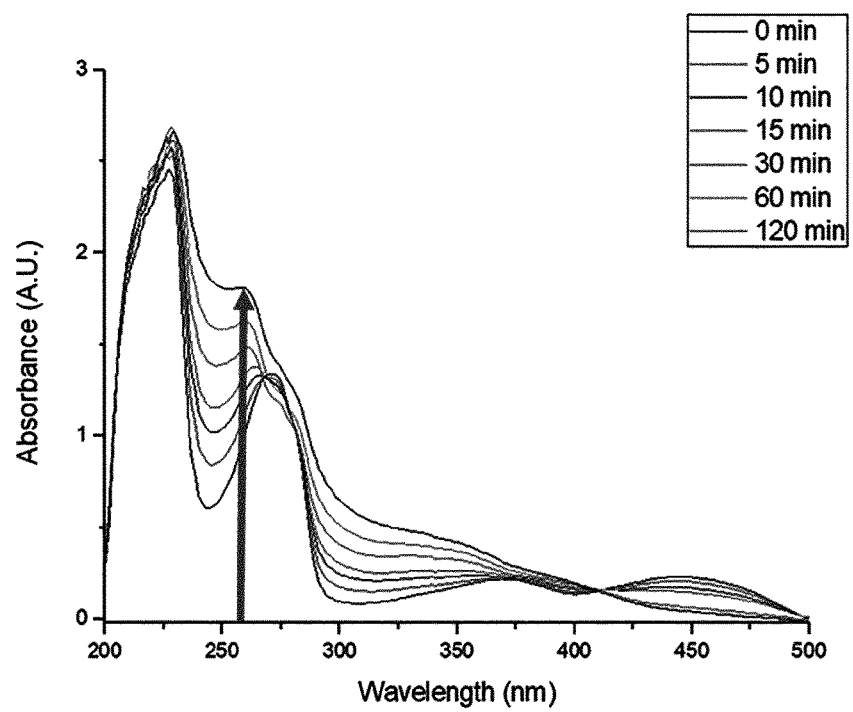
[Fig. 6]
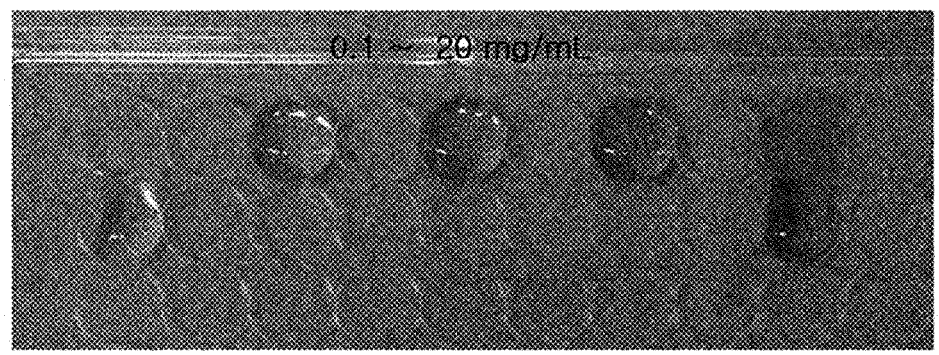

[Fig. 7]
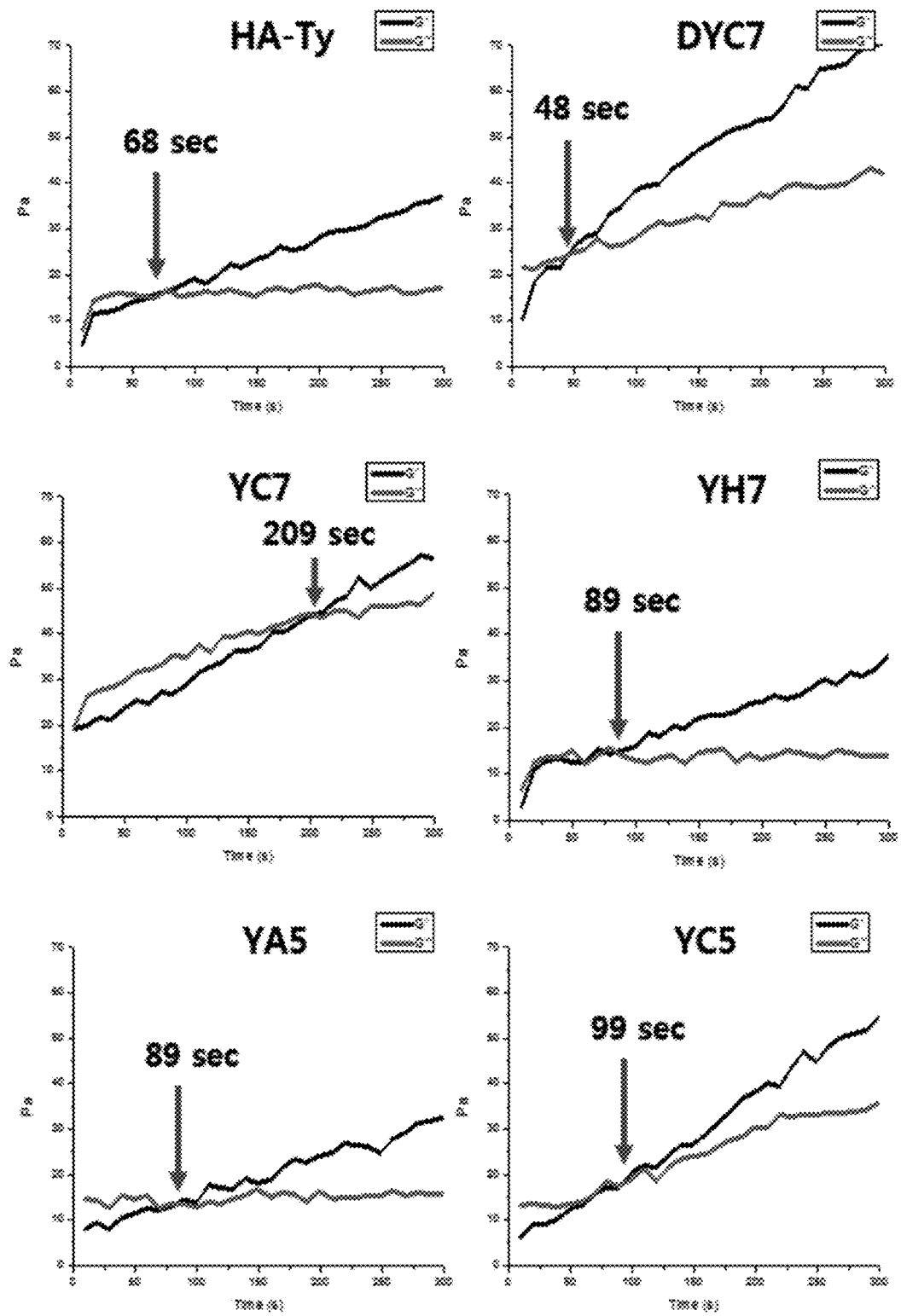

[Fig. 8]
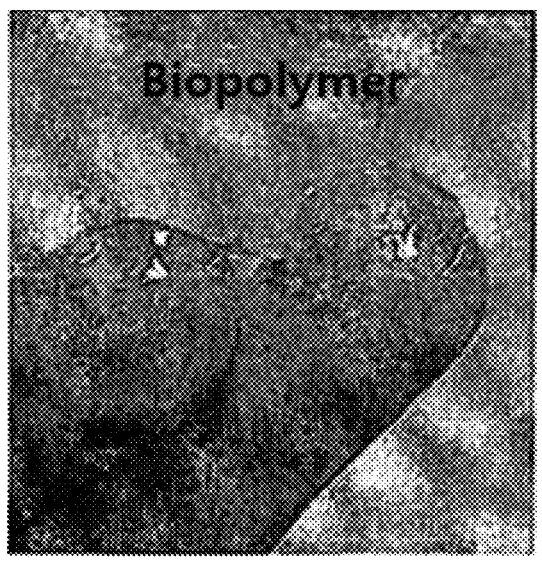 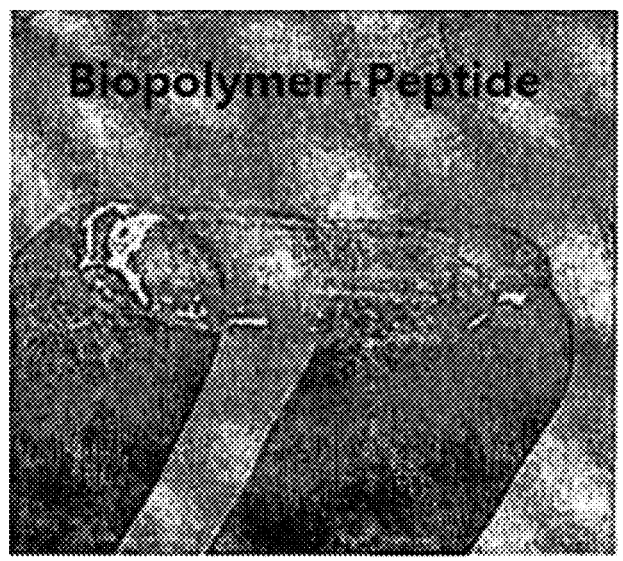

[Fig. 9]
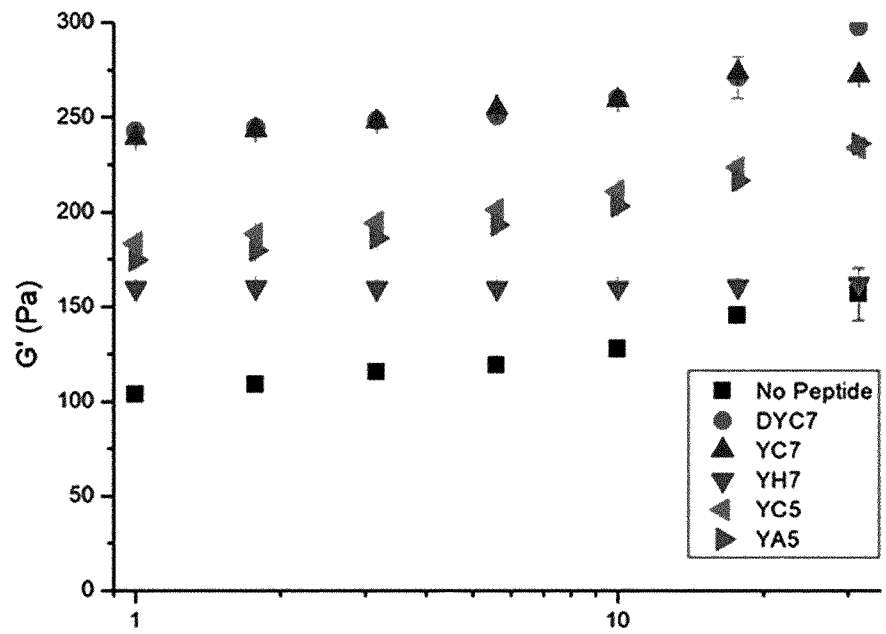
[Fig. 10]
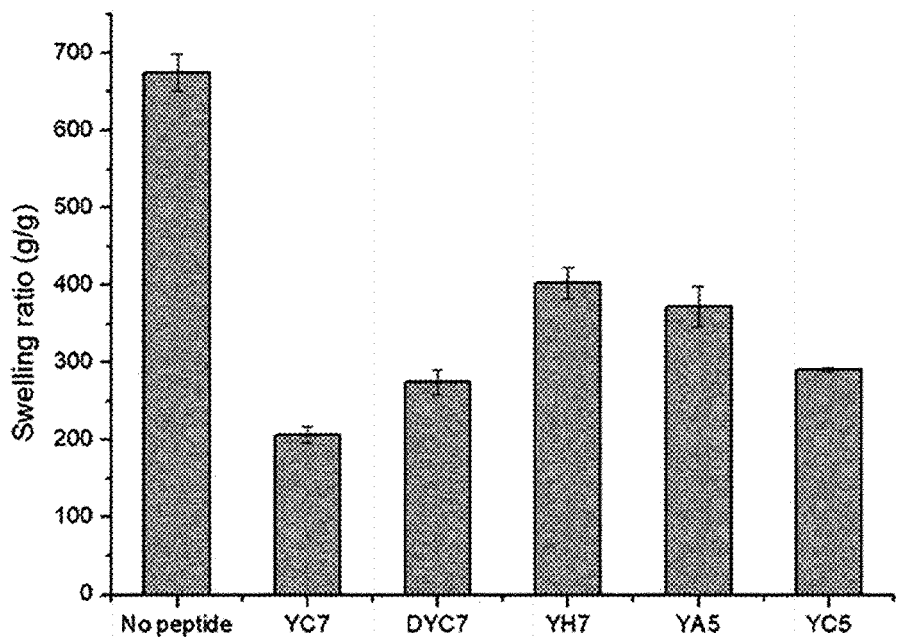

[Fig. 11]
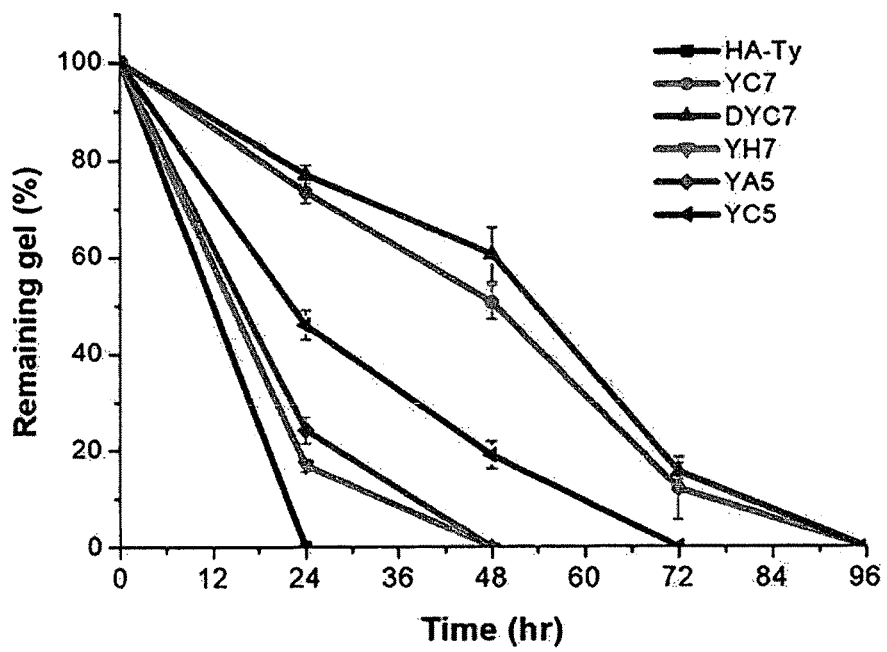
[Fig. 12]
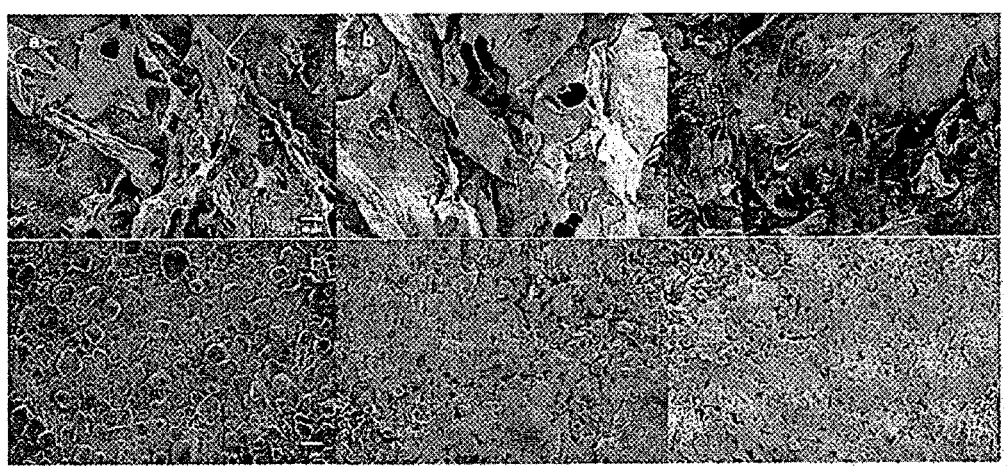

[Fig. 13]
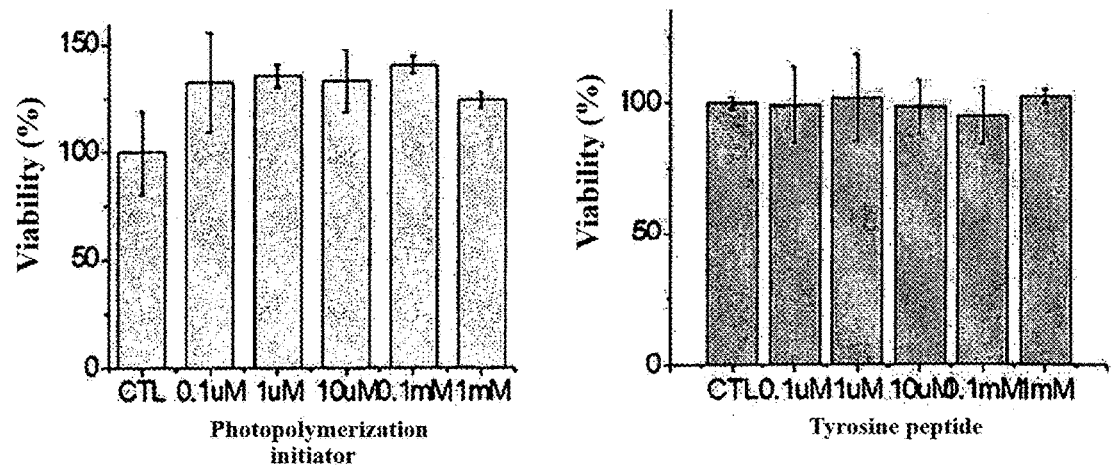
[Fig. 14]
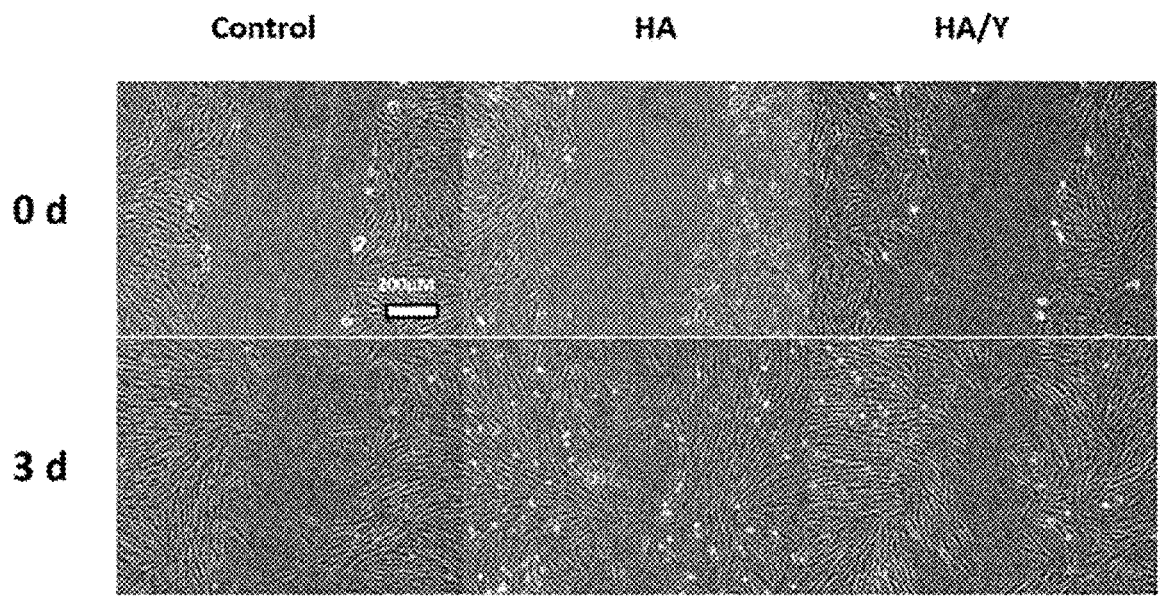

[Fig. 15]
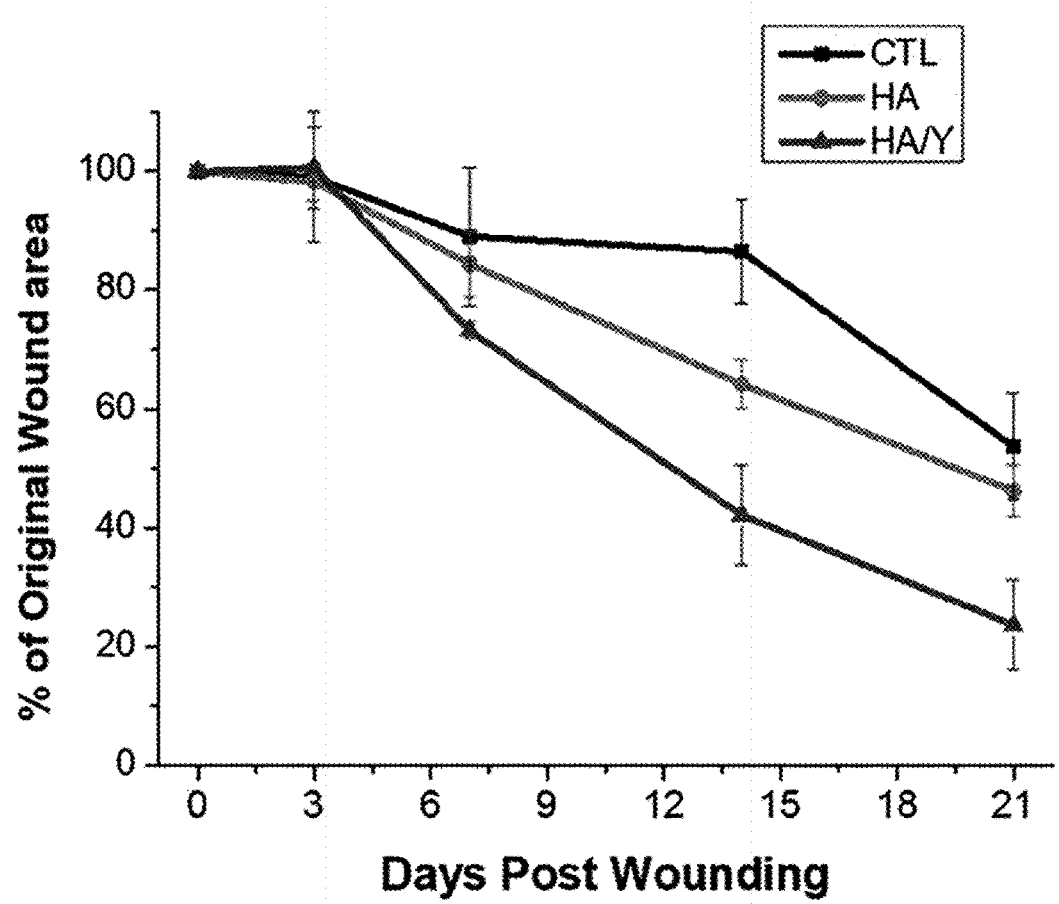

[Fig. 16]
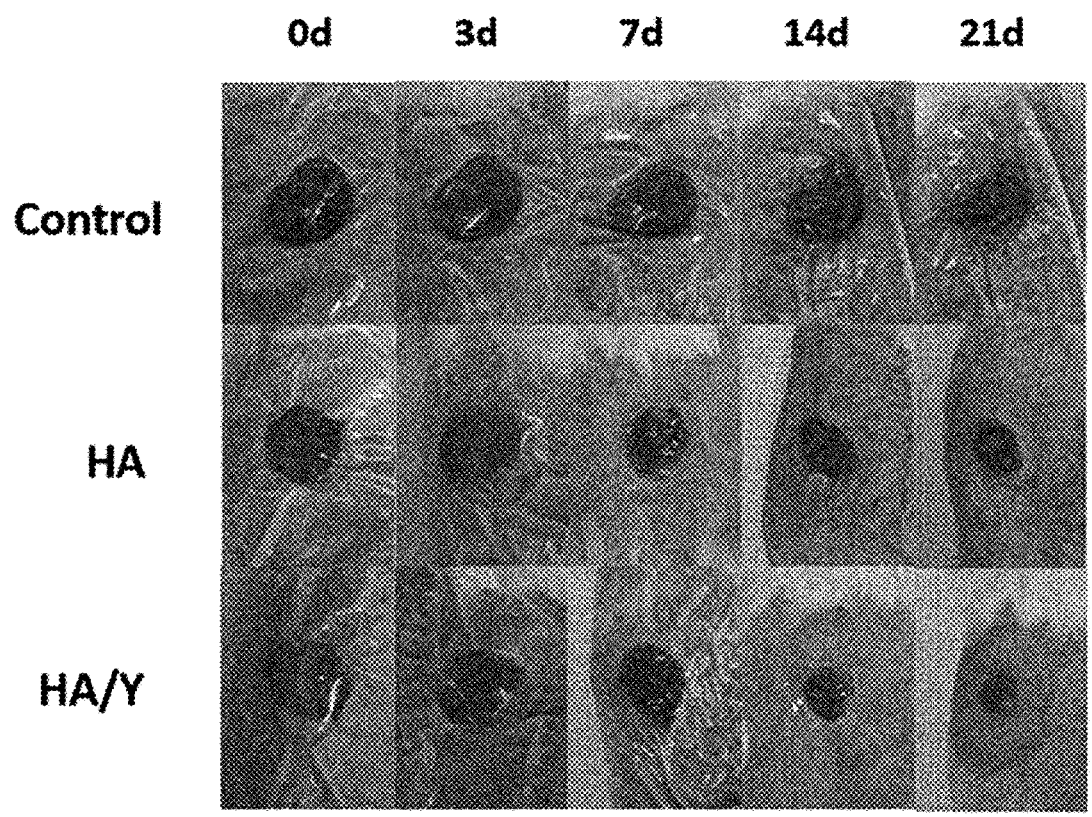
[Fig. 17]
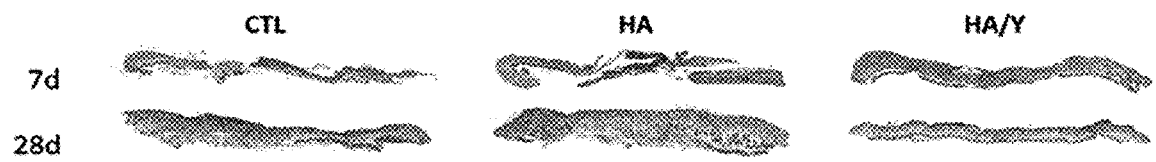

[Fig. 18]
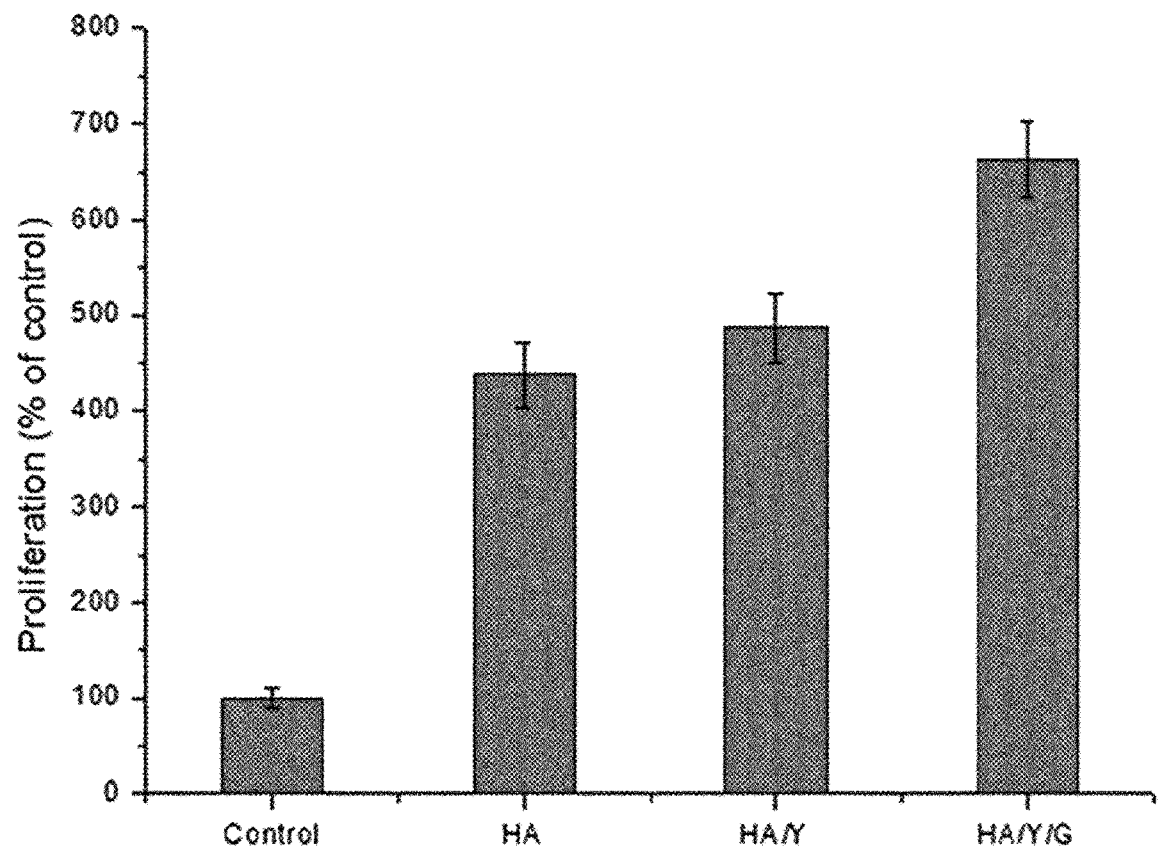

[Fig. 19]
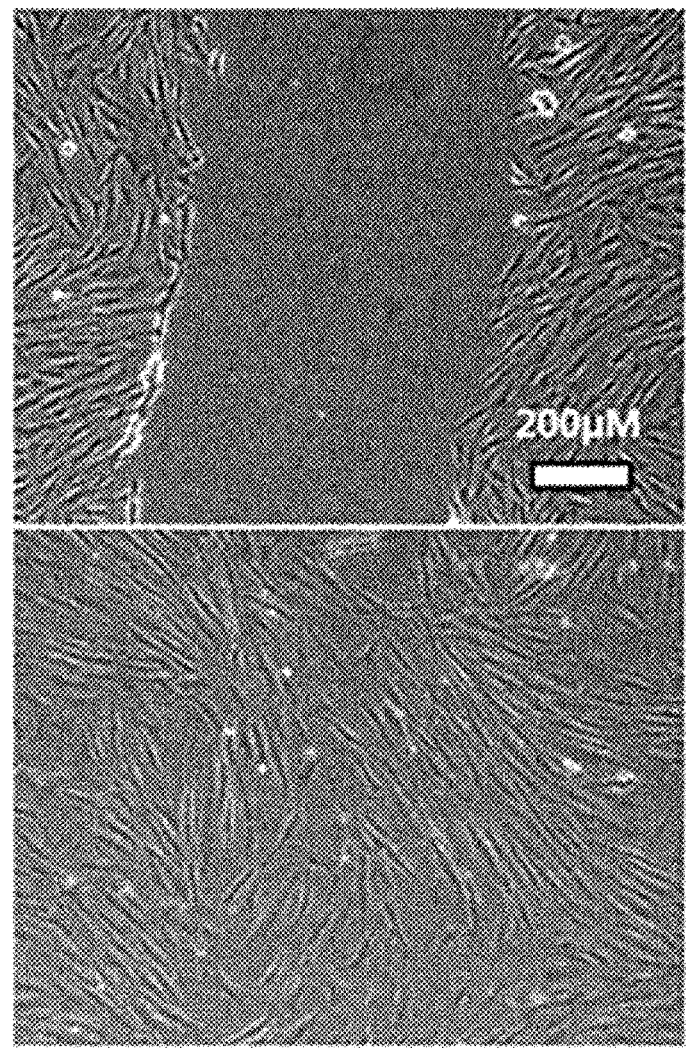

TYROSINE PEPTIDE CROSS-LINKED BIOCOMPATIBLE HYDROGEL AND METHOD OF PRODUCTION

CROSS-REFERENCE TO RELATED APPLICATIONS

This application is a continuation of Application No. PCT/KR2017/011973, filed Oct. 27, 2017 which in turn claims the benefit of Korean Patent Application No. 10-2016-0141147, filed Oct. 27, 2016, the disclosures of which are incorporated by reference into the present application.

SEQUENCE LISTING

A SEQUENCE LISTING is submitted in a file named PUS190026 ST25.TXT via EFS Web and is hereby incorporated by reference in its entirety. Said file was created on Dec. 24, 2020 and is 2,006 bytes in size.

TECHNICAL FIELD

The present disclosure relates to a biocompatible biopolymer-based hydrogel as a functional biomaterial produced by crosslinking in the presence of a photopolymerization initiator and a method for producing the same.

BACKGROUND ART

Hydrogels are used as scaffolds or artificial extracellular matrices that provide growth spaces for cells from the viewpoint of tissue engineering. The scaffolds or artificial extracellular matrices allow cells to grow better or in desired directions for the purpose of tissue engineering. In this context, biopolymer-based hydrogels have high utility in biomedical applications.

Various kinds of polysaccharides such as glycogen, chitosan, cellulose, and hyaluronic acid are known as biopolymers. These biopolymers are converted into hydrogels by physical crosslinking or irreversible chemical crosslinking. For example, irreversible chemical crosslinking of a biopolymer is performed by introducing functional groups (such as thiol, catechol, and phenol groups) to exposed moieties (such as amine and carboxyl groups) of the biopolymer through chemical bonding and crosslinking these functional groups. An enzyme or photopolymerization initiator may be used for this crosslinking. The functional groups meet the active sites of the enzyme, are structurally modified, and participate in crosslinking. When irradiated with light of an optimal wavelength, the photopolymerization initiator becomes photosensitive to produce free radicals, which induce crosslinking of the moieties.

In connection with the use of enzyme, a method for fabricating a hydrogel by crosslinking in the presence of horseradish peroxidase (HRP) can be found in Korean Patent Publication No. 2010-0076173. According to this method, the reaction rate is easy to control and a highly biocompatible hydrogel is provided. Further, the method inevitably involves the use of a toxic promoter such as hydrogen peroxide ($H_2O_2$) in addition to the enzyme. The toxic promoter may deteriorate the bioaffinity of the hydrogel. Attempts have been made to provide elastic hydrogels using metal ligand complexes as polymerization initiators instead of enzymes can be found in the literature (see Korean Patent Publication No. 2016-0026441 and Yang et al. Biomacromolecules 2015, 16, 3819-3826). One of the metal ligand complexes is $Ru(II)(bpy)_3^{2+}$. Ruthenium is a heavy metal used in the industry and is thus unsuitable for in vivo and in vitro use. That is, ruthenium is not considered biocompatible.

Thus, there is a need to provide a method for fabricating a biocompatible hydrogel in a simple manner without using toxic materials or metals and an elastic hydrogel adapted to various shapes in both in vivo and in vitro applications, affording effective wound dressing or tissue adhesion prevention.

DISCLOSURE

Technical Problem

It is one object of the present invention to provide a biocompatible hydrogel that is suitable for bioapplications and is elastic so as to be adapted to various shapes in both in vivo and in vitro applications, achieving maximum effects on wound healing such as wound dressing and tissue adhesion prevention. It is another object of the present invention to provide a method for producing the hydrogel in a simple manner.

Technical Solution

One aspect of the present disclosure provides a method for producing a biocompatible hydrogel, including: coupling a biopolymer with an amine group-containing phenolic compound to provide an amidated biopolymer; mixing the amidated biopolymer with a monophenolic compound and a tyrosine-based peptide represented by YY—X—YY (SEQ IDs: 1-3) (wherein each Y is a tyrosine residue and X is a mono- (SEQ ID: 1), di- (SEQ ID: 2), or tripeptide (SEQ ID: 3), each consisting of one, two, or three amino acid residues, respectively, out of 20 amino acid residues) to prepare a mixture solution; and mixing the mixture solution with a photopolymerization initiator, followed by photocuring to form a structure in which the amidated biopolymer molecules are bonded through a dityrosine linker.

A further aspect of the present disclosure provides a biocompatible hydrogel having a structure in which biopolymer molecules are coupled with an amine group-containing phenolic compound at both ends and are directly bonded through a dityrosine linker or are bonded through two or more dityrosine linkers connected via a tyrosine-based peptide moiety.

Another aspect of the present disclosure provides a biocompatible hydrogel having a structure in which a biopolymer molecule is coupled with an amine group-containing phenolic compound at one end and terminal functional groups introduced into another molecule of the biopolymer are connected to a dityrosine linker at the other end wherein the biopolymer molecules are directly bonded through a dityrosine linker or are bonded through one or more dityrosine linkers connected via a tyrosine-based peptide moiety.

Advantageous Effects

According to exemplary embodiments, the use of the naturally existing photopolymerization initiator enables the production of a biocompatible hydrogel without causing any toxicity problem. In addition, the hydrogel produced by the method of the present invention is elastic due to their increased storage modulus. Therefore, the hydrogel is adapted to various shapes in both in vivo and in vitro applications.

BRIEF DESCRIPTION OF THE DRAWINGS

FIG. 5 shows a change in the absorbance of a tyramine-conjugated biopolymer prepared in accordance with one embodiment of the present invention during hydrogel formation.

FIG. 6 shows photographs demonstrating an effective concentration of a photopolymerization initiator through a tilt test.

FIG. 7 shows crosslinking times of hyaluronic acid-tyramine hydrogels.

FIG. 8 compares the elasticity of a hydrogel produced without the addition of a tyrosine-rich peptide and that of a hydrogel produced with a tyrosine-rich peptide.

FIG. 9 shows the storage moduli of hyaluronic acid-tyramine hydrogels composed of no peptide and tyrosine-rich peptides having different sequences according to exemplary embodiments of the present invention.

FIG. 10 shows the swelling ratios of hyaluronic acid-tyramine hydrogels containing no peptide and peptides having different sequences according to exemplary embodiments of the present invention.

FIG. 11 shows the degradation degrees of hydrogels containing tyrosine-based peptides having different sequences according to exemplary embodiments of the present invention.

FIG. 12 shows SEM images of a biopolymer (a) before and (b) after crosslinking and (c) after crosslinking with a tyrosine-rich peptide.

FIG. 13 shows the viabilities of cells used in a cytotoxicity test.

FIG. 14 shows the cytotoxicity of hydrogel components used in a cell proliferation test.

FIG. 15 compares the effects of hydrogels on wound healing based on wound areas.

FIG. 16 shows photographs of wound healing process with different hydrogels.

FIG. 17 confirms time-dependent wound recovery rates analyzed by using Masson's trichrome staining.

FIG. 18 is a histogram comparing the results of proliferation tests on dermal fibroblasts after incubation of wound healing peptide GHK-Cu.

FIG. 19 shows the effect of a hydrogel according to one embodiment of the present invention as a functional scaffold, which was confirmed through a proliferation test on dermal fibroblasts after incubation of wound healing peptide GHK-Cu.

BEST MODE

The present invention will now be described in detail with reference to the accompanying drawings.

The present invention intends to provide a method for producing a biocompatible hydrogel using a naturally existing photopolymerization initiator without causing no toxicity problem and a hydrogel with increased storage modulus that is soft so as to be adapted to various shapes in both in vivo and in vitro applications. For reference, conventional a crosslinked hyaluronic acid produced by crosslinking hyaluronic acid alone in the presence of riboflavin has insufficient scaffold performance. The present inventors have found that dityrosine linkages can be sufficiently formed by a crosslinking mechanism with ultraviolet light in the presence of riboflavin. Based on this finding, the present inventors have continued research and finally arrived at the present invention.

The present invention provides a soft biocompatible hydrogel produced by irreversible crosslinking of a biopolymer with light in the presence of a photopolymerization initiator. The biopolymer is preferably treated with a compound having specific functional groups at both ends for the purposes of enhancing the storage modulus, complex viscosity, and binding force of the hydrogel. This treatment mechanism can be represented as follows:

[Reaction mechanism 1]

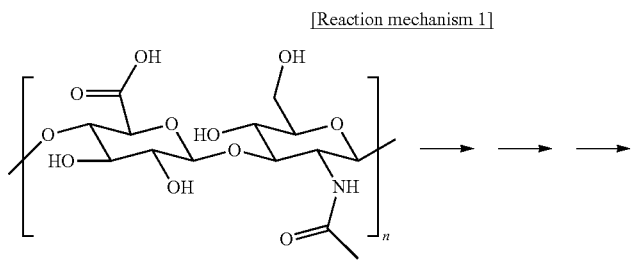

(10~1200 kDa)

-continued

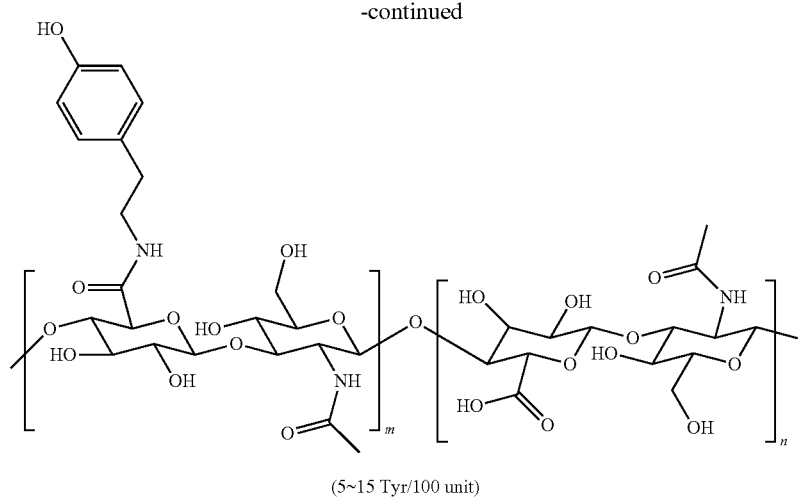

(5~15 Tyr/100 unit)

Figure 1:
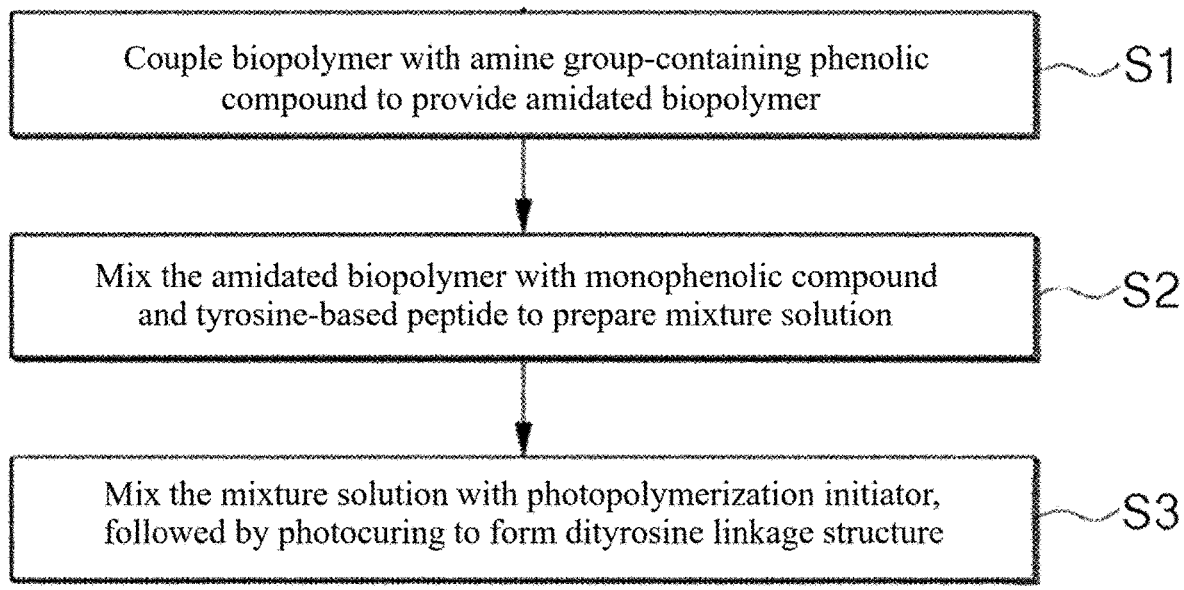
FIG. 1 is a flowchart illustrating a method for producing a biocompatible hydrogel according to one embodiment of the present invention.

FIG. 1 is a flowchart illustrating a method for producing a biocompatible hydrogel according to one embodiment of the present invention. Referring to FIG. 1, in S1, a biopolymer is coupled with an amine group-containing phenolic compound to provide an amidated biopolymer.

The amine group-containing phenolic compound may be, for example, a compound that has an amine group as a functional group forming an amide bond with the biopolymer at one end and a hydroxyl or quinone group as a functional group forming a dityrosine linkage at the other end. The formation of the dityrosine linkage will be described below. The amine group-containing phenolic compound is preferably tyramine, meta-tyramine or dopamine that has both at least one amine group forming an amide bond and at least one hydroxyl group forming a dityrosine linkage. Particularly preferred is tyramine that is biocompatible and acts as a bridge of the dityrosine linkage, which will be described below.

The amine group-containing phenolic compound may be used in an amount ranging from 5 units or more, 5 to 15 units or 10 to 13 units per 100 repeating units of the biopolymer. Within this range, the amine group-containing phenolic compound can effectively act as a bridge (see FIGS. 2 and 3).

The biopolymer is selected from the group consisting of polysaccharides and biodegradable polymers. Examples of the polysaccharides include glycogen, cellulose, heparin, alginate, hyaluronic acid, and chitosan. Examples of the biodegradable polymers include poly(D,L-lactide-co-glycolide), poly(lactic acid), poly(glycolic acid), poly(ε-caprolactone), poly(α-valerolactone), poly(β-hydroxybutyrate), and poly(β-hydroxyvalerate). As can be seen from the Examples section that follows, the biopolymer may be hyaluronic acid having a molecular weight of 10 to 1200 kDa. However, there is no restriction on the kind and molecular weight of the biopolymer.

Figure 2:
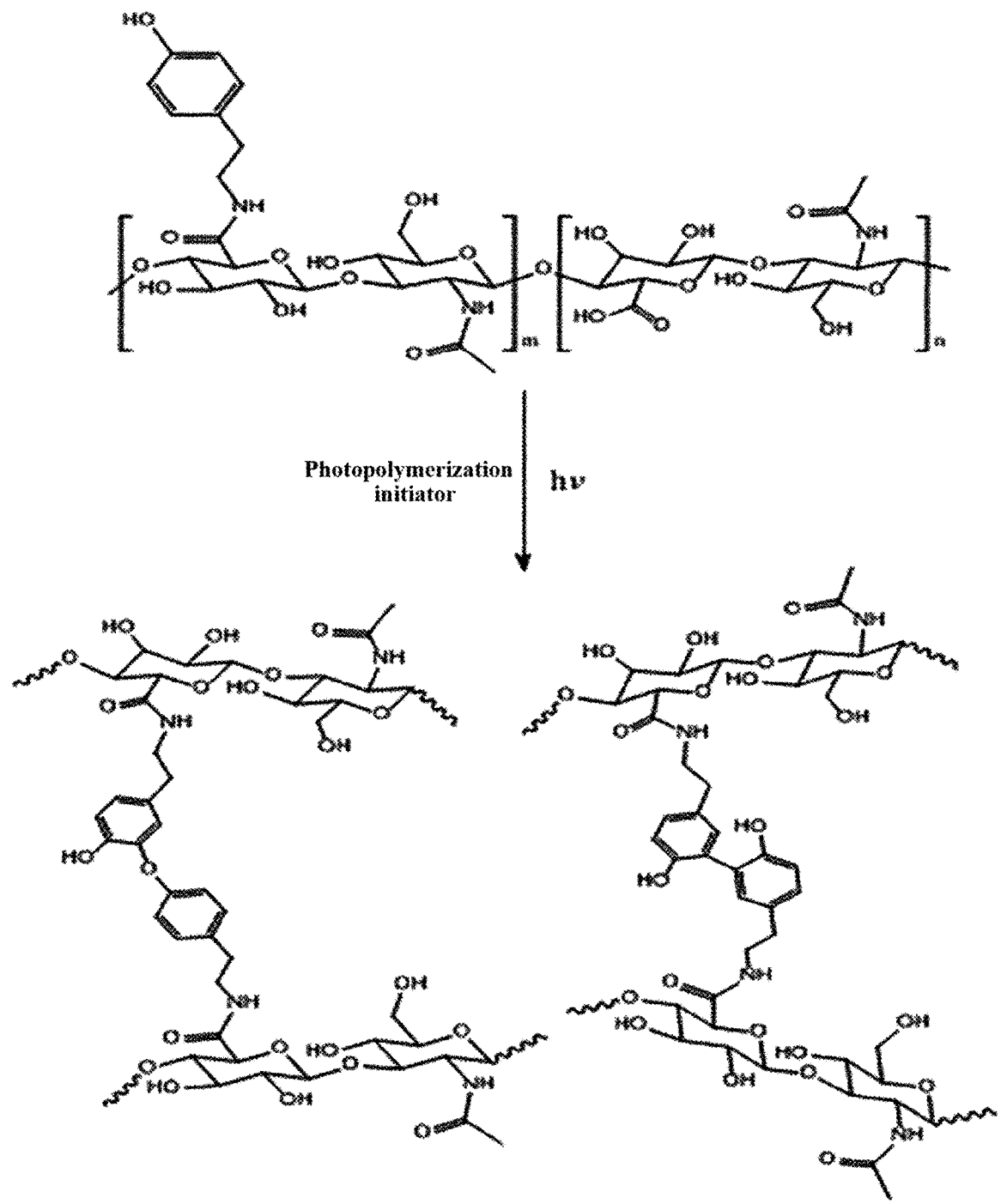
FIG. 2 shows a reaction mechanism in which tyramine as an amine group-containing phenolic compound is introduced as a dityrosine crosslinking bridge into hyaluronic acid as a biopolymer.

For reference, FIG. 2 shows a reaction mechanism for the production of the hydrogel by crosslinking of the tyramine-conjugated biopolymer with light (e.g., UV light) in the presence of a photopolymerization initiator. As shown in FIG. 2, the hydrogel has a structure in which the amidated biopolymer molecules at both ends are bonded through a dityrosine linker. The formula shown at the bottom right of FIG. 2 represents the amidated biopolymer molecules bonded through a dityrosine linker. The formula shown at the bottom left of FIG. 2 represents the amidated biopolymer molecules bonded through a catechol linker similar to the dityrosine linker.

Figure 3:
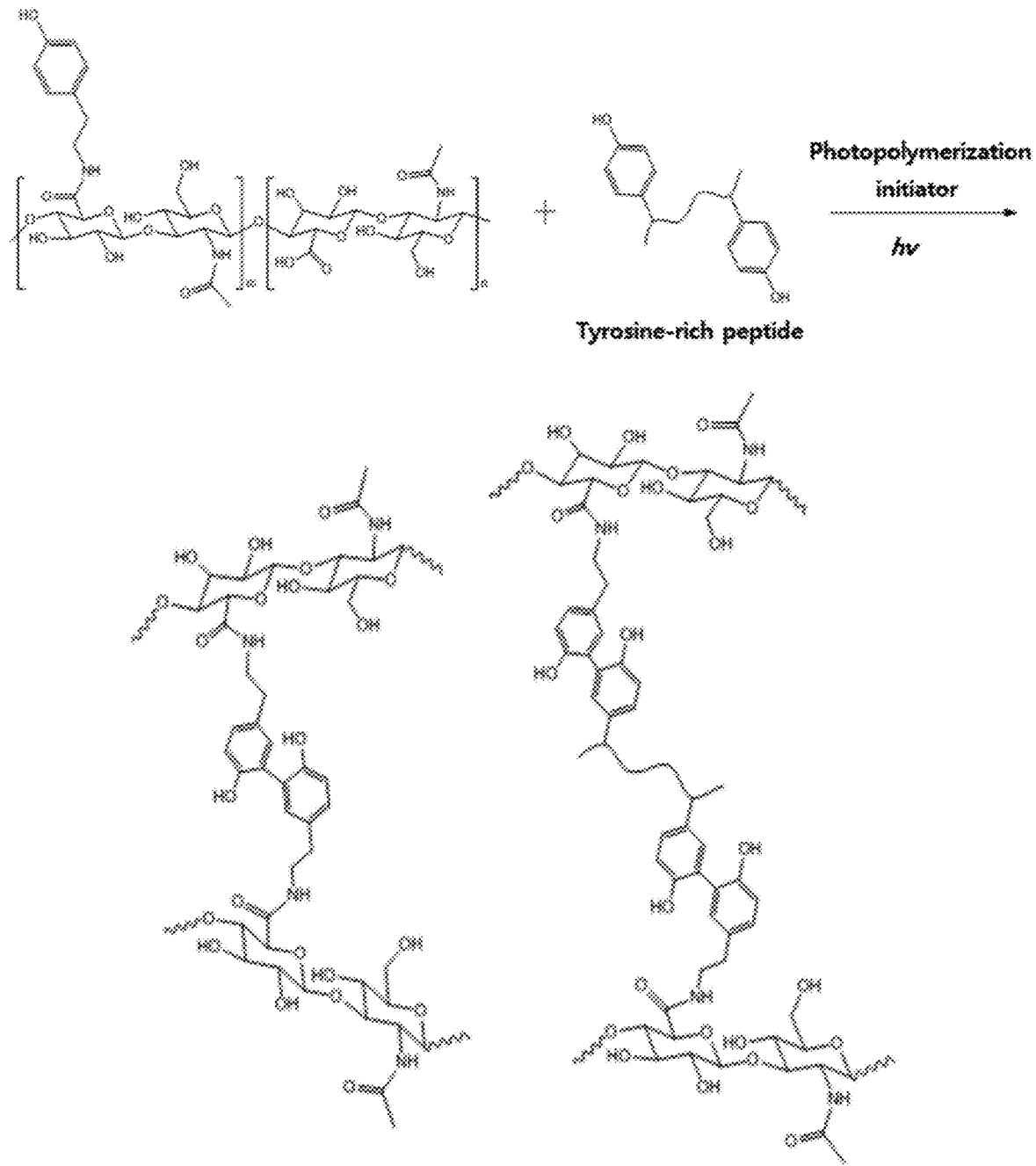
FIG. 3 shows a reaction mechanism in which a tyrosine-based peptide is added to the tyramine-conjugated hyaluronic acid prepared in FIG. 2, followed by photocuring with ultraviolet light in the presence of riboflavin as a photopolymerization initiator to form a structure in which the tyramine-conjugated hyaluronic acid molecules are bonded through a dityrosine linker.

The method of the present invention is characterized in that the tyramine-conjugated biopolymer is mixed with a tyrosine-based peptide before crosslinking in the presence of a photopolymerization initiator. This reaction mechanism is shown in FIG. 3. The first reaction product shown in FIG. 3 has a structure in which the tyramine-conjugated biopolymer molecules are directly bonded through a dityrosine linker without any intermediate linkage. The second reaction product shown in FIG. 3 has a structure in which dityrosine linkers are connected via a tyrosine-based peptide moiety. The tyrosine-based peptide moiety can be released from the second reaction product by a phenoloxidase such as tyrosinase or laccase, secreted by cells in bio-environments and plays its role when applied in vivo.

In S2, the amidated biopolymer is mixed with a monophenolic compound and a tyrosine-based peptide represented by YY—X—YY (SEQ IDs: 1-3) (wherein each Y is a tyrosine residue and X is a mono- (SEQ ID: 1), di- (SEQ ID: 2), or tripeptide (SEQ ID: 3), each consisting of one, two, or three amino acid residues, respectively, out of 20 amino acid residues) to prepare a mixture solution. The monophenolic compound acts on crosslinking sites of the tyrosine-based peptide. For example, the monophenolic compound may be at least one selected from the group consisting of phenol, para-cresol, and para-isooctylphenol. Para-cresol or para-isooctylphenol is preferred due to its reactivity.

The tyrosine-based peptide acts to connect the dityrosine linkers, which will be described below. The tyrosine-based peptide is preferably a tyrosine-rich peptide that can enhance the storage modulus of the hydrogel.

For example, the tyrosine-based peptide may be selected from the group consisting of YYACAYY (SEQ ID: 4), di-YYACAYY (SEQ ID: 5), YYAHAYY (SEQ ID: 6), YYAYY (SEQ ID: 7), YYCYY (SEQ ID; 8), and combinations thereof (wherein each Y is a tyrosine residue, each A is alanine (Ala), each C is cysteine (Cys), and H is histidine (His)). When each of the peptides is added, the tyrosine (Y) residues can induce crosslinking with the phenol groups introduced into the biopolymer, and as a result, a peptide/biopolymer mixed hydrogel can be produced by a phenol oxidase in vivo, resulting in increases in the storage modulus and complex viscosity of the hydrogel (see FIGS. 5 to 8).

YYACAYY (SEQ ID: 4), YYAHAYY (SEQ ID: 6), YYAYY (SEQ ID: 7), and YYCYY (SEQ ID; 8) can be used in view of solubility.

The amidated biopolymer, the monophenolic compound, the tyrosine-based peptide, and the photopolymerization initiator are preferably present in a weight ratio of 90-95:2-6:0.5-5:0.5-5. This weight ratio is optimum for curing the hydrogel.

In S3, the mixture solution is mixed with a photopolymerization initiator, followed by photocuring to form a structure in which the amidated biopolymer are bonded through a dityrosine linker.

The method of the present invention is characterized in that the photocuring is performed by irradiation with ultraviolet light in the presence of riboflavin as a bio friendly photopolymerization initiator. Riboflavin, a vitamin B2 derivative, has been used to treat the cornea due to the ability to synthesize collagen when exposed to light. Since surplus riboflavin is excreted in urine, riboflavin causes no side effects even when overdosed and is thus considered as a biocompatible substance. In conclusion, riboflavin is preferred as a photopolymerization initiator for biocompatible biopolymers.

Examples of preferred photopolymerization initiators for the production of the biocompatible hydrogel include riboflavin, ferrocene, and anthraquinone.

The concentration of the photopolymerization initiator can be determined by a tilt test, as exemplified in FIG. 6. Specifically, the concentration of the photopolymerization initiator may vary from 0.02 to 4 mM.

For example, the hydrogel may have a structure in which the amidated biopolymer molecules are directly bonded through a dityrosine linker or are bonded through two or more dityrosine linkers connected via the tyrosine-based peptide moiety.

The photocuring can be performed using ultraviolet light of a 300 nm wavelength band such as 365 nm in the presence of riboflavin as the photopolymerization initiator (see FIG. 5).

At least one of the width, thickness, and length of the hydrogel may be from 1 μm to 10 mm.

For example, the biocompatible hydrogel produced by the method of the present invention may have a structure in which biopolymer molecules are coupled with an amine group-containing phenolic compound at both ends and are directly bonded through a dityrosine linker or are bonded through two or more dityrosine linkers connected via a tyrosine-based peptide moiety.

The hydrogel including aminated biopolymer molecules directly bonded through a dityrosine linker can be represented by Formula 1:

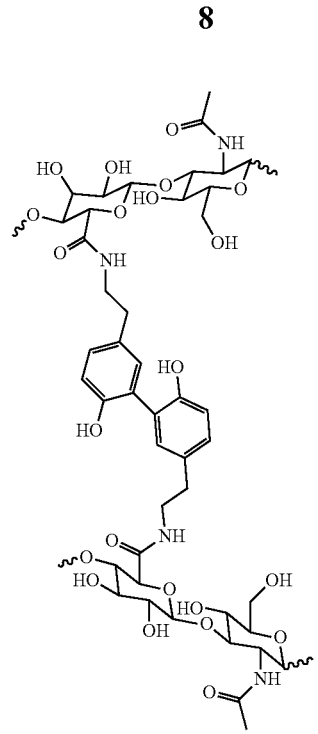

[Formula 1]

The hydrogel including aminated biopolymer molecules bonded through two or more dityrosine linkers connected via a tyrosine-based peptide moiety can be represented by Formula 2:

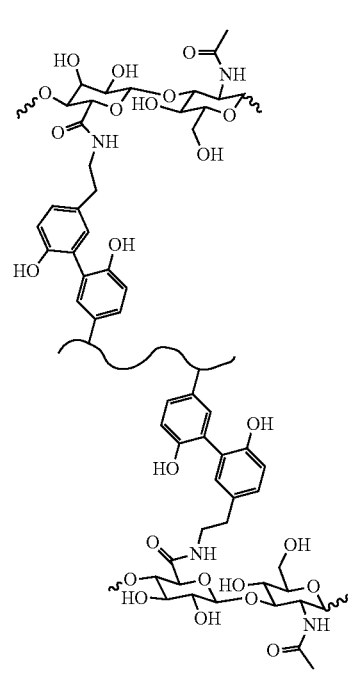

[Formula 2]

As another example, the biocompatible hydrogel produced by the method of the present invention may have a structure in which a biopolymer molecule is coupled with an amine group-containing phenolic compound at one end and terminal functional groups introduced into another molecule of the biopolymer are connected to a dityrosine linker at the other end wherein the biopolymer molecules are directly bonded via the dityrosine linker or are bonded through one or more dityrosine linkers connected via a tyrosine-based peptide moiety.

The hydrogel including aminated biopolymer molecules directly bonded through a dityrosine linker can be represented by Formula 3:

[Formula 3]

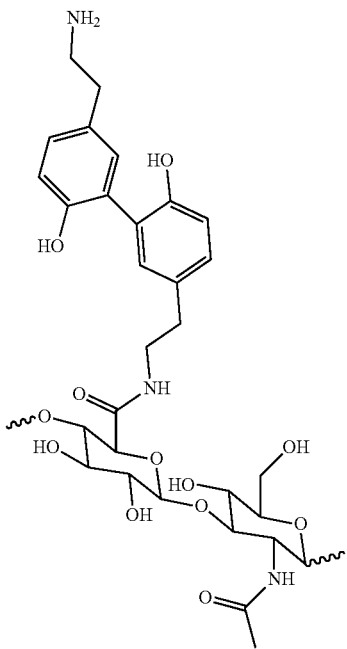

The hydrogel including aminated biopolymer molecules bonded through one or more dityrosine linkers connected via a tyrosine-based peptide moiety can be represented by Formula 4:

[Formula 4]

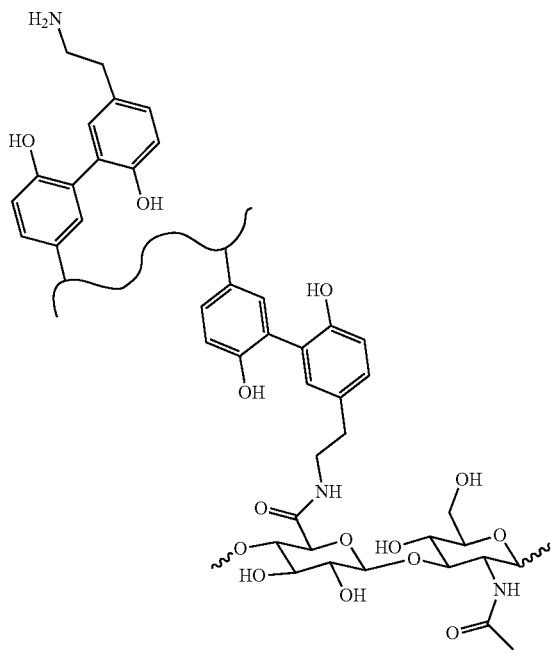

The hydrogel is biocompatible and may be a dityrosine crosslinked structure having a storage modulus of 100 to 300 Pa, as measured at an oscillation frequency of 1 Hz and an angular velocity of 10 to 100 rad/s. The hydrogel may be a dityrosine crosslinked structure having a complex viscosity of 0 to 250 Pa·s, as measured at an oscillation frequency of 1 Hz and an angular velocity of 10 to 100 rad/s. The hydrogel may be a dityrosine crosslinked structure having a loss modulus of 0 to 100 Pa, as measured at an oscillation frequency of 1 Hz and an angular velocity of 10 to 100 rad/s.

The hydrogel can be utilized as a functional scaffold for wound dressing or tissue adhesion prevention. The hydrogel may optionally further include at least one wound healing factor selected from the group consisting of GHK-Cu, cell growth factors, and antioxidants. At least one of the width, thickness, and length of the hydrogel may be from 1 μm to 10 mm.

Referring to FIG. 8, a hydrogel produced by crosslinking hyaluronic acid alone is vulnerable to tearing due to its low elasticity (see the left image of FIG. 8), whereas the elasticity of the peptide-added hyaluronic acid hydrogel was observed even with the naked eye (see the right image of FIG. 8).

The addition of the tyrosine-rich peptide allows the use of the hyaluronic acid hydrogel produced by crosslinking with ultraviolet light in the presence of riboflavin for wound dressing or tissue adhesion prevention without losing its elasticity (see FIGS. 9 to 11). The hyaluronic acid based hydrogel can be used as a functional bioscaffold for functional factors effective in wound healing (for example, GHK-Cu, cell growth factors, and antioxidants) (see FIGS. 18 and 19).

For reference, UV irradiation conditions suitable for use in the present invention are 115 V, 60 Hz, 0.7 A, 8 W, and 254 to 365 nm. UV light can be irradiated for 10 to 120 minutes.

The amine group-containing compound-conjugated biopolymer may be used in an amount of 0.5 to 1.5% by weight. The tyrosine-based peptide and the riboflavin photopolymerization initiator may be used at concentrations of 0.01 to 0.5 mM and 0.02 to 4 mM, respectively.

The following non-limiting experiments serve to illustrate the invention.

EXAMPLES

Material Preparation

Hyaluronic acid (sodium salt, Mw 1200 kDa) was provided from SK Bioland (Korea) and purchased from Lifecore Biomedical. N-(3-Dimethylaminopropyl)-N'-ethylcarbodiimide hydrochloride 98% (EDC), riboflavin 5'-phosphate sodium, 3-(4,5-dimethylthiazol-2-yl)-2,5-diphenyltetrazoluim bromide, hyaluronidase and thermolysin were purchased from Sigma Aldrich. N-Hydroxysulfosuccinimide sodium salt was purchased from TCI, and tyramine hydrochloride, 99% was purchased from Acros Organics. Dulbecco's Modified Eagle's Medium (DMEM) and phosphate buffer saline (PBS) were purchased from Welgene and fetal bovine serum was purchased from BeadTech. UV irradiation was performed by LightningCure 2000 (Hamamatsu, Japan), and rheometric analysis was performed by Discovery Hybrid Rheometer-3 (TA Instruments).

Example 1

Preparation of Hyaluronic Acid-Tyramine Conjugates

Hyaluronic acid-tyramine (HA-Ty) conjugates were prepared via EDC/NHS coupling method (FIG. 2). Hyaluronic acid sodium salt (1.0 g, 2.5 mmol carboxylic acid groups) was dissolved in 100 mL of distilled water (0.01 mol/L). To the solution were added EDC (1437.75 mg, 7.5 mmol), NHS (863.175 mg, 7.5 mmol), and tyramine hydrochloride (1302.3 mg, 7.5 mmol). The resulting solution was stirred overnight at room temperature. The reaction mixture was purified by sequential ultrafiltration (MWCO 12000) with 5 L of NaCl solution (100 mmol/L), EtOH solution (18 mol/L), and 5 L of distilled water, respectively.

Figure 4:
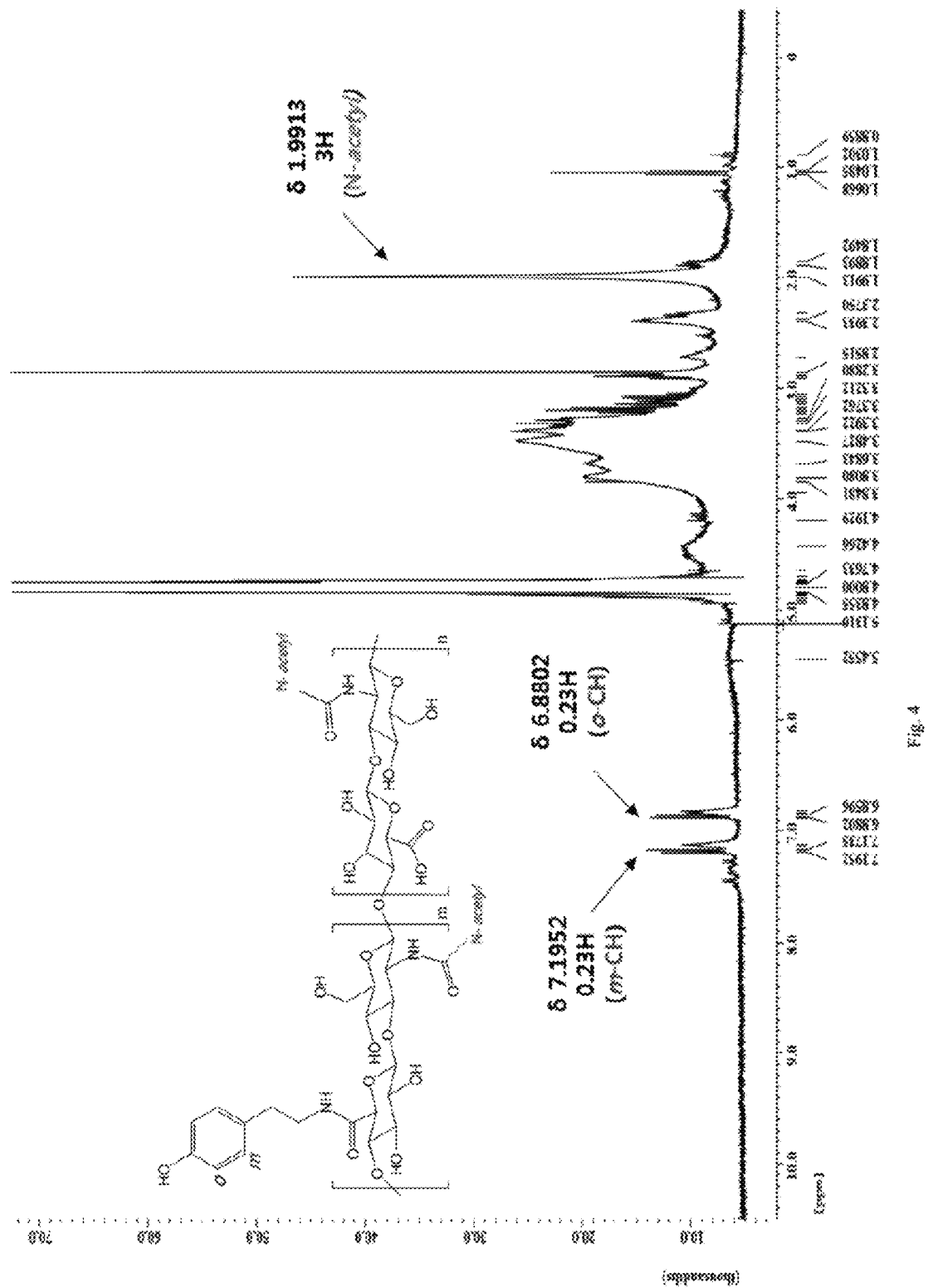
FIG. 4 is an NMR spectrum showing the tyramine introduction ratio of the presence of tyramine moieties in a tyramine-conjugated biopolymer prepared in accordance with one embodiment of the present invention.

The resulting HA-Ty conjugate was collected as a white powder after freeze-drying. The conjugation of tyramine in the HA-Ty conjugate was confirmed by NMR. The results are summarized in FIG. 4. The degree of substitution of tyramine residues in HA-Ty conjugate, defined as the number of tyramine residues per 100 repeating units of hyaluronic acid, was calculated to be 11, which was determined by $^1$H NMR ($D_2O$): δ 1.99 (acetylmethyl protons), 6.8 and 7.2 (aromatic protons of tyramine residues) (see FIG. 4).

Conjugation of tyramine to the carboxylic acid of hyaluronic acid was once again confirmed by UV spectroscopy. Tyramine hydrochloride was dissolved in PBS buffer at pH 7.4, diluted to 0.1 μM-10 μM, followed by ultraviolet absorption survey scans. The results are summarized in FIG. 5. As shown in FIG. 5, a distinctive UV absorbance was observed at 274 nm.

Preparation of biocompatible hydrogel-1 Hydrogels were prepared by photocrosslinking of the tyramine-conjugated hyaluronic acid. HA-Ty conjugate (1.5 wt %) was dissolved in PBS buffer (pH 7.4), sufficiently mixed with riboflavin as a photopolymerization initiator, and irradiated with 365 nm ultraviolet light. An optimum concentration (0.1-20 mg/mL) of riboflavin was determined by performing a tilt test (see FIG. 6). Absorbances were recorded at designated time points during the photocrosslinking. An increase in the absorbance of new peaks at 260 nm was observed (see FIGS. 2 and 5).

Preparation of Biocompatible Hydrogel-2

Hydrogels were prepared by photocrosslinking of tyrosine containing peptides and hyaluronic acid. First, 1.5 wt % of HA-Ty was dissolved in PBS buffer (pH 7.4) and 5 kinds of tyrosine-based peptides (YYACAYY (SEQ ID: 4) (YC7), di-YYACAYY (SEQ ID: 5) (DYC7), YYAHAYY (SEQ ID: 6) (YH7), YYAYY (SEQ ID: 7) (YA5), and YYCYY (SEQ ID; 8) (YC5), 0.1 mM each) were added to the HA-Ty solution to prepare a total of four mixture solutions.

Specifically, tyrosine-rich peptide sequences (YYACAYY (SEQ ID: 4), di-YYACAYY (SEQ ID: 5), YYAYY (SEQ ID: 7), YYCYY (SEQ ID; 8)/0.01-1 mM) were added to the HA-Ty solution and riboflavin as a photopolymerization initiator (0.1-1 mg/mL) was sufficiently mixed with the mixture solutions. The resulting mixtures were irradiated with 365 nm ultraviolet light (see FIG. 3).

<Evaluation of Physical Properties>

1) Analysis of Crosslinking Time and Storage Modulus (G')

The crosslinking time and storage modulus (G') were analyzed using a rheometer. Hydrogel samples with 20 mm diameter and 5 mm thickness were prepared. The crosslinking time was measured over time at an oscillation frequency of 1 Hz and a stress sweep of 10 Pa. The storage modulus was measured at an oscillation frequency of 1 Hz and a stress sweep of 1-100 Pa. All measurements were performed in triplicate and averaged.

Specifically, the storage modulus G' was obtained by oscillatory shear measurements at room temperature using a constant stress rheometer (Discovery Hybrid Rheometer-3 from TA Instruments, USA). For the measurements, hydrogel samples with a defined shape of 20 mm diameter and 5 mm thickness were prepared. The cured hydrogel was placed on a lower rheometer stage, and an upper rheometer fixture (diameter 20 mm) was lowered until it made contact with the top surface of the sample. The value of G' was then measured at oscillation frequency 1 Hz in a stress sweep test of 1-100 Pa. This stress sweep was performed in order to determine the limit of the linear viscoelastic range. All the G' measurements were obtained in triplicate. Error bars in figures represent the standard deviation from the mean value (see FIGS. 7 and 9). As can be seen from FIGS. 7 and 9, the addition of the tyrosine-based peptides retarded the curing time and increased the storage modulus.

2) Swelling and Degradation Tests

Swelling and degradation tests on the hydrogels were conducted by the following procedures. First, HA hydrogels were photocrosslinked with different peptide sequences (YYACAYY (SEQ ID: 4), di-YYACAYY (SEQ ID: 5), YYAYY (SEQ ID: 7), YYCYY (SEQ ID; 8), and YYAHAYY (SEQ ID: 6), 0.1 mM each). Swelling experiments were performed by measuring the increase in weight of the lyophilized hydrogels. Lyophilized hydrogels were placed in 1 mL distilled water at 25° C. The swelling ratio (S %) of hydrogels in distilled water was calculated using S %=[($W_t$−$W_0$)/$W_0$)]100, where $W_t$ is the weight of the swollen hydrogel at time t, and $W_0$ is the weight of the dry gel at time 0. Degradation tests were performed by measuring the weights of hydrogels in PBS containing 0.01 mg/mL hyaluronidase at different time points.

Specifically, it is well known that the mechanical properties of hydrogels are closely related to the crosslinking density. The storage modulus (G') measured by rheological analysis is a reliable value representing the rigidity of the subjected hydrogel. The G' of HA-Ty hydrogel without any peptide addition was 156.6 Pa at a strain of 1% at 30 rad/s (see FIG. 10). Addition of tyrosine-based peptides increased the G' of hydrogels, indicating that the peptides were able to strengthen the hydrogel by increasing its crosslinking density.

The G' values of DYC7 (297.6 Pa) and YC7 (271.8 Pa) were almost twice the value of HA-Ty hydrogel. YH7 peptide which has only one amino acid difference from YC7 showed almost the same G' as HA-Ty at 30 rad/s.

These results indicate that the degree of crosslinking of HA-Ty is not dependent on the length of the tyrosine-based peptide, but on the specific sequence. This matches with the result of YA5 and YC, where the G' of these two cases were higher than that of YH7 even though they were shorter in length.

Similar cases were also observed in the swelling properties of the hydrogels (see FIG. 10). Swelling behavior of hydrogel is another indicator of the level of crosslinking density, which is inversely related to the rheological measurements.

As expected, YC7 showed the least swelling ratio (206.6) compared to HA-Ty alone (674. 6). Most of the results were as predicted. DYC7 showed the highest G' but its swelling ratio was found to be slightly higher than that of YC7. These results are as predicted due to the partial insolubility of DYC7, indicating that its portion was not involved in crosslinking. The undissolved peptide remained precipitated to cause an increase in G'. The degradation test results also revealed similar patterns (see FIG. 10). While most of the HA-Ty hydrogels were completely dissolved in 24 hr, the degradation rates of hydrogels prepared by crosslinking with tyrosine-based peptides were slowed down (see FIG. 11). Along with the swelling property, YC7 and DYC7 were found to be most suitable for controlling HA-Ty hydrogels.

The following additional tests were carried out using YC7.

3) Scanning Electron Microscopy of the Hydrogels

Lyophilized hydrogel samples were analyzed by scanning electron microscopy. Non-crosslinked hyaluronic acid gel particles existed independently, whereas crosslinked hyaluronic acid hydrogel particles were self-assembled. Hydrogels were added with tyrosine-based peptide (YY-ACAYY (SEQ ID: 4)) in 0.1 mM concentration. FIG. 12 shows SEM images of the biopolymer (a) before and (b) after crosslinking and (c) after crosslinking with the tyrosine-rich peptide. As revealed in FIG. 12, when crosslinked with the tyrosine-based peptide, the particles were assembled without losing their morphology.

4) Cytotoxicity of the Hydrogels

To investigate the biocompatibility of the hydrogels, fibroblasts were used in a cytotoxicity test. Fibroblasts were seeded with the density of $4 \times 10^4$/well in 24 well plates. After 1 day, serum starvation was performed for 2 hr, and then cells were incubated with riboflavin (0.1 μM-10 mM) and YC7 (0.1 μM-1 mM) for 24 hr at 37° C. Finally, cell toxicity was evaluated by MTT assay. Fibroblasts were grown with the density of $1 \times 10^5$/well in 12 well dishes to test their proliferation in different hydrogels. The grown cells area was scratched using pipette tips to create a wound-like environment and the hydrogels were added to 12 transwells, which were then placed in the dishes where cells had been grown. The proliferation effect of cells was evaluated depending on the degree of cell filling in the scratches. The results are shown in FIGS. 13 and 14. As can be seen from FIGS. 13 and 14, riboflavin and YC7 had no cytotoxicity against the cells irrespective of their concentrations. More cells proliferated in the hydrogels than in the control.

5) Effects of the Hydrogels on Wound Healing in Mouse Wound Models

Mouse wound models were used to investigate the effects of the hydrogels on wound healing. Wild type Balb/c mice (5 weeks of age) were used for wound healing models. A punch biopsy tool was used to create wounds. Tegaderm (3M) was used as a control. The wounds were covered with the hydrogels, which were also covered with Tegaderm. The degree of wound healing and the area of the wound site were evaluated by photographs. As a result, HA/Y had a superior effect on wound healing. The results are shown in FIGS. 15 and 16. The superior wound healing effect of HA/Y appeared because the tyrosine-based peptide of HA/Y delayed the swelling and degradation of the hydrogel, allowing the hydrogel to stay longer at the wound site.

Based on the effects of the hydrogels on wound healing using the mouse wound models, the tissue recovery states of the models were also confirmed using Masson's trichrome staining. Tissues were collected at designated time points and fixed in animal fixing solution for 24 hr. The fixing solution was replaced with PBS before storage. Thereafter, the tissue was cut into sections and analyzed by Masson's trichrome staining. The results are shown in FIG. 17. As can be seen from FIG. 17, the hydrogel containing the tyrosine-based peptide showed better wound healing results.

6) Confirmation of Efficacy of the Hydrogel Scaffold Using Functional Additive

Cell experiments were conducted to simply confirm whether a hydrogel added with GHK-Cu (wound healing peptide) as a functional additive was effective in enhancing wound healing. Human dermal fibroblasts were used and proliferation tests were performed by seeding the cells ($1 \times 10^5$/well) in 12 well dishes. The histogram (FIG. 18) was obtained using MTT assay. The cell images (FIG. 19) were obtained using scratch assay.

Based on FIGS. 18 and 19, the role of the produced hydrogel as a functional scaffold was confirmed. The hydrogel without GHK-Cu showed a fourfold increase in cell proliferation compared to the control. The addition of the GHK-Cu increased the cell proliferation by a factor of at least sixfold. These results suggest that the hydrogel containing GHK-Cu can be utilized as a biomaterial for wound healing.

According to the conventional crosslinking mechanism by an enzyme such as tyrosinase, phenol groups are converted to quinone groups followed by a larger number of complex reaction steps. Compare to the photocrosslinking, the use of tyrosinase leads to the formation of hydrogels with comparable or slightly inferior physical properties.

INDUSTRIAL APPLICABILITY

The hyaluronic acid based hydrogel produced by crosslinking with ultraviolet light in the presence of riboflavin is expected to be a useful biomaterial that acts as a scaffold, containing various bioactive substances including GHK-Cu, in various fields. The biocompatible hydrogel of the present invention is applicable to tissue engineering, even surgically and clinically relevant medical fields. In addition, the biocompatible hydrogel of the present invention can be used in various biomedical applications, including hydration, wound healing, antifouling, the formation of artificial tissues (e.g., artificial cartilage), and adhesion prevention.

The invention claimed is:

1. A method for producing a biocompatible hydrogel, comprising: coupling a biopolymer with an amine group-containing phenolic compound to provide an amidated biopolymer; mixing the amidated biopolymer with a monophenolic compound and a tyrosine-based peptide represented by YY-A-YY (SEQ ID NOs: 1-3), wherein each Y is a tyrosine residue, A is X (SEQ ID NO: 1), A is XX (SEQ ID NO: 2), or A is XXX (SEQ ID NO: 3), wherein each X consists of a single amino acid residue, and X is selected from the group consisting of alanine (Ala), cysteine (Cys), histidine (His), and tyrosine (Tyr), to prepare a mixture solution; and mixing the mixture solution with a photopolymerization initiator, followed by photocuring to form a structure in which the amidated biopolymer molecules are bonded through a dityrosine linker.

2. The method according to claim 1, wherein the amidated biopolymer molecules are directly bonded through a dityrosine linker or are bonded through two or more dityrosine linkers connected via the tyrosine-based peptide moiety.

3. The method according to claim 1, wherein the tyrosine-based peptide is at least one selected from the group consisting of YYACAYY (SEQ ID NO: 4), di-YYACAYY (SEQ ID NO: 5), YYAHAYY (SEQ ID NO: 6), YYAYY (SEQ ID NO: 7), and YYCYY (SEQ ID NO: 8), wherein in SEQ ID NOs: 4-8 each Y is a tyrosine residue, each A is an alanine (Ala) residue, each C is a cysteine (Cys) residue, and H is a histidine (His) residue.

4. The method according to claim 1, wherein the amine group-containing phenolic compound is at least one selected from the group consisting of tyramine, meta-tyramine, and dopamine and is used in an amount of 5% by weight or more per 100 repeating units of the biopolymer.

5. The method according to claim 1, wherein the biopolymer is a polysaccharide selected from the group consisting of glycogen, cellulose, heparin, alginate, hyaluronic acid, and chitosan or a biodegradable polymer selected from the group consisting of poly(D,L-lactide-co-glycolide), poly(lactic acid), poly(glycolic acid), poly(ε-caprolactone), poly(σ-valerolactone), poly(β-hydroxybutyrate), and poly(β-hydroxyvalerate).

6. The method according to claim 1, wherein the monophenolic compound is at least one selected from the group consisting of phenol, para-cresol, and para-isooctylphenol.

7. The method according to claim 1, wherein the amidated biopolymer, the monophenolic compound, the tyrosine-based peptide, and the photopolymerization initiator are present in a weight ratio of 90-95:2-6:0.5-5:0.5-5.

8. The method according to claim 1, wherein the photopolymerization initiators is selected from the group consisting of riboflavin, ferrocene, anthraquinone, and mixtures thereof.

* * * * *

SEQUENCE LISTING

```
<160> NUMBER OF SEQ ID NOS: 8

<210> SEQ ID NO 1
<211> LENGTH: 5
<212> TYPE: PRT
<213> ORGANISM: Artificial Sequence
<220> FEATURE:
<223> OTHER INFORMATION: Synthesized
<220> FEATURE:
<221> NAME/KEY: misc_feature
<222> LOCATION: (3)..(3)
<223> OTHER INFORMATION: Xaa is selected from the group consisting of
```

Ala, Cys, His, and Tyr

<400> SEQUENCE: 1

Tyr Tyr Xaa Tyr Tyr
1               5

<210> SEQ ID NO 2
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: misc_feature
<222> LOCATION: (3)..(4)
<223> OTHER INFORMATION: Xaa is selected from the group consisting of
      Ala, Cys, His, and Tyr

<400> SEQUENCE: 2

Tyr Tyr Xaa Xaa Tyr Tyr
1               5

<210> SEQ ID NO 3
<211> LENGTH: 7
<212> TYPE: PRT
<213> ORGANISM: Artificial Sequence
<220> FEATURE:
<223> OTHER INFORMATION: Synthesized
<220> FEATURE:
<221> NAME/KEY: misc_feature
<222> LOCATION: (3)..(5)
<223> OTHER INFORMATION: Xaa is selected from the group consisting of
      Ala, Cys, His, and Tyr

<400> SEQUENCE: 3

Tyr Tyr Xaa Xaa Xaa Tyr Tyr
1               5

<210> SEQ ID NO 4
<211> LENGTH: 7
<212> TYPE: PRT
<213> ORGANISM: Artificial Sequence
<220> FEATURE:
<223> OTHER INFORMATION: Synthesized

<400> SEQUENCE: 4

Tyr Tyr Ala Cys Ala Tyr Tyr
1               5

<210> SEQ ID NO 5
<211> LENGTH: 14
<212> TYPE: PRT
<213> ORGANISM: Artificial Sequence
<220> FEATURE:
<223> OTHER INFORMATION: Synthesized

<400> SEQUENCE: 5

Tyr Tyr Ala Cys Ala Tyr Tyr Tyr Tyr Ala Cys Ala Tyr Tyr
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Synthesized

<400> SEQUENCE: 6

```
Tyr Tyr Ala His Ala Tyr Tyr
1               5

<210> SEQ ID NO 7
<211> LENGTH: 5
<212> TYPE: PRT
<213> ORGANISM: Artificial Sequence
<220> FEATURE:
<223> OTHER INFORMATION: Synthesized

<400> SEQUENCE: 7

Tyr Tyr Ala Tyr Tyr
1               5

<210> SEQ ID NO 8
<211> LENGTH: 5
<212> TYPE: PRT
<213> ORGANISM: Artificial Sequence
<220> FEATURE:
<223> OTHER INFORMATION: Synthesized

<400> SEQUENCE: 8

Tyr Tyr Cys Tyr Tyr
1               5
```